United States Patent
Dunham et al.

(12) 
(10) Patent No.: US 6,385,292 B1
(45) Date of Patent: May 7, 2002

(54) SOLID-STATE CT SYSTEM AND METHOD

(75) Inventors: Bruce M. Dunham, Mequon; John Scott Price, Wauwatosa, both of WI (US); Colin R. Wilson, Niskayuna, NY (US); Douglas Snyder, Brookfield, WI (US)

(73) Assignee: GE Medical Systems Global Technology Company, LLC, Waukesha, NY (US)

( * ) Notice: Subject to any disclaimer, the term of this patent is extended or adjusted under 35 U.S.C. 154(b) by 0 days.

(21) Appl. No.: 09/751,110

(22) Filed: Dec. 29, 2000

(51) Int. Cl.⁷ .................................................. H01J 35/00
(52) U.S. Cl. ........................................... 378/122; 378/9
(58) Field of Search ............................... 378/122, 4–20

(56) References Cited

U.S. PATENT DOCUMENTS 5,729,583 A * 3/1998 Tang ........................... 378/122
5,995,585 A 11/1999 Salasoo

* cited by examiner

Primary Examiner—Craig E. Church
(74) Attorney, Agent, or Firm—Peter J. Vogel

(57) ABSTRACT

A solid state x-ray source (14) for a computed tomograph (CT) imaging system (10) is presented. X-ray source (14) has a cathode (58) which is preferably formed of a plurality of addressable elements. The cathode is positioned within a vacuum chamber (74) so that electrodes emitted thereby impinge upon anode (68) spaced apart from cathode (58). An electron beam (82) is formed and moved along the length of cathode (58). The anode (68) is disposed within a cooling block portion (58) and operatively adjacent to an x-ray transmissive window (66). The anode (68) and x-ray transmissive window (66) are disposed within an elongated channel (64) of the cooling block portion (56).

20 Claims, 3 Drawing Sheets

SOLID-STATE CT SYSTEM AND METHOD

TECHNICAL FIELD

The present invention relates generally to computed tomograph (CT) imaging and, more particularly, to a x-ray source utilized in connection with CT systems.

BACKGROUND ART

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector. A scintillator is located adjacent the collimator, and photodiodes are positioned adjacent the scintillator.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two slice detector has two rows of detector elements, and a four slice detector has four rows of detector elements. During a multislice scan, multiple rows of detector cells are simultaneously impinged by the x-ray beam, and therefore data for several slices is obtained.

A system that does not require a rotating x-ray source is described in U.S. Pat. Nos. 4,521,900 and 4,521,901. In the '900 patent, a large vacuum chamber is used which incorporates an electron gun and ring-shaped targets to produce x-rays. The electron beam emerges from the gun several feet away from the patient, travels a bent path to move toward the targets then hits the material to produce x-rays. The single fairly high power electron beam sweeps out a circle, a ring that surrounds the patient, to produce the "scan" effect. One drawback to such a system is that a large vacuum system to enclose the electron beam's path or trajectory is required, and further, a complicated beam deflection system is employed to accurately steer the beam.

Accordingly, it would be desirable to provide a CT scanner and CT scanner system that provides a x-ray source that reduces the complexity of the scanning system and does not require a rotating x-ray source.

SUMMARY OF THE INVENTION

It is therefore one object of the invention to provide a solid state x-ray tube to reduce the complexity of the x-ray tube. In one aspect of the invention, a CT system comprises a solid state x-ray source for a computed tomograph (CT) imaging system is illustrated. X-ray source has a cathode which is preferably formed of a plurality of addressable elements. The cathode is positioned within a vacuum chamber so that electrons emitted thereby impinge upon anode spaced apart from cathode. An electron beam is formed and moves along the length of cathode. The anode is disposed within a cooling block portion and operatively adjacent to an x-ray transmissive window. The anode and x-ray transmissive window are disposed within an elongated channel of the cooling block portion.

Advantageously, the present invention uses cold-cathode technology. The employment of cold-cathode technology allows the possibility for an electron beam source to be turned on and off very quickly with the limitation being the switching speed of the associated electronic and optical circuitry. In addition, fast electronic gating circuits may allow many of these emitting sources to be switched sequentially, thus allowing an electron beam to sweep a target. Such technology will allow the typically rotating x-ray source in a CT system to be removed which substantially removes the complexity associated therewith. For example, bearing issues, target balancing problems, and Z-axis growth problems are associated with prior known CT systems. Also, the prior known systems are complex to service.

Another advantage of the invention is that the use of solid state components eliminates the need for a large vacuum system and a complicated beam deflection system. Other eliminated features compared to the prior art include not requiring a rotating target, a filament heater circuit and motors, and the large support frames associated with a rotating target.

Another advantage of the invention is that because of the fast scan times, applications that require fast scan times such as cardiac imaging may be employed.

Yet another advantage of the invention is that slip rings commonly used in a rotating system may be eliminated. Slip ring connections typically introduce noise and complexity into the transmission of signals obtained from the detectors as well as transmitting power and high voltage to the x-ray source.

Another advantage of the invention is that because of high heat dissipation enabled with a stationary anode, the usual massive target with massive graphite backing is not required to store heat generated by electrons that come to rest in the target. Furthermore, this will greatly reduce or eliminate the need to wait for the X-ray tube to cool.

Another advantage of the invention is that shielding necessary for canceling the effect of the earth's magnetic field is not required.

Other objects and advantages of the present invention will become apparent upon the following detailed description and appended claims, and upon reference to the accompanying drawings.

DETAILED DESCRIPTION OF THE PREFERRED EMBODIMENT

Figure 1:
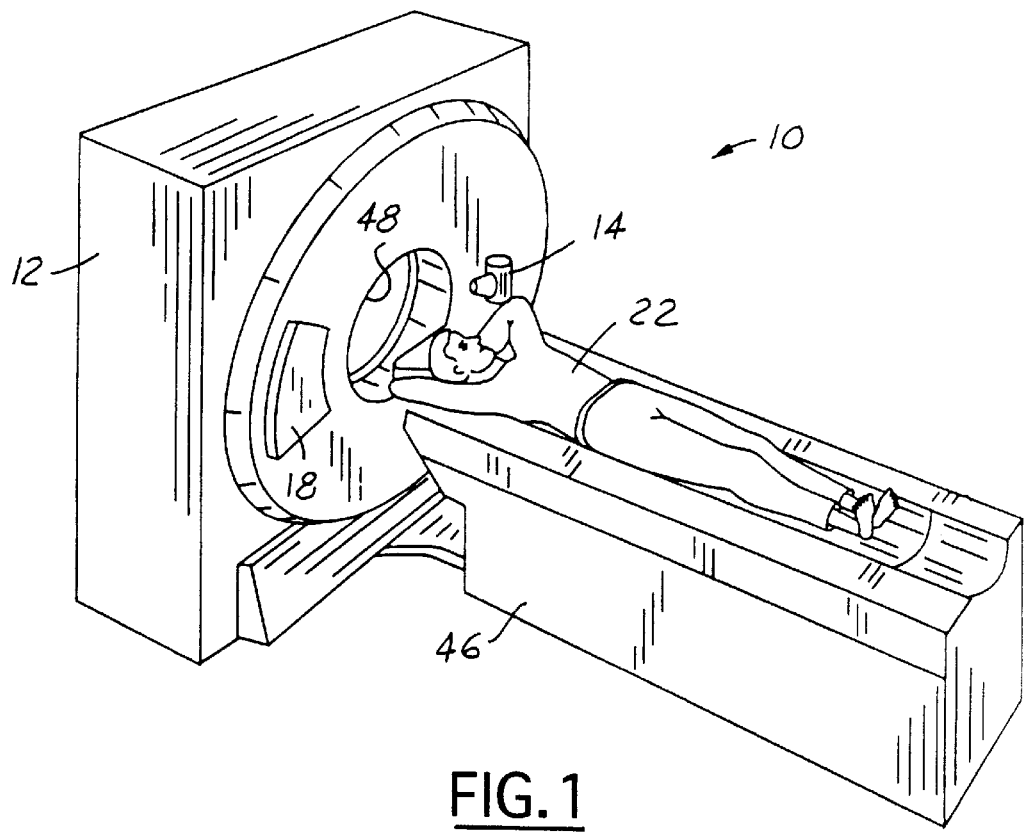
FIG. 1 is a pictorial view of a CT imaging system according to the present invention.
Figure 2:
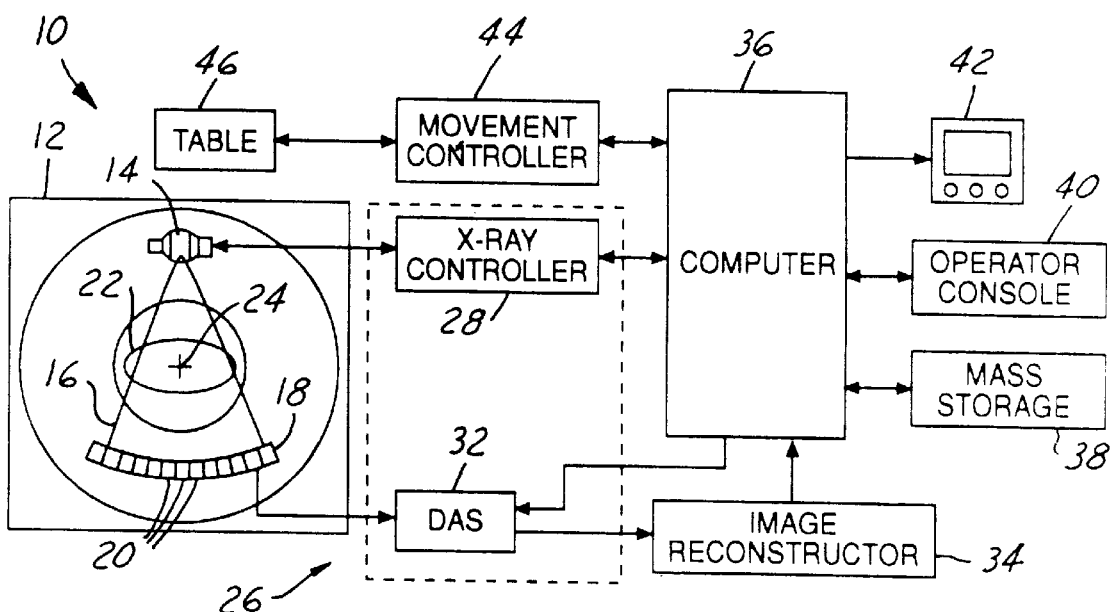
FIG. 2 is a block schematic diagram of the system illustrated in FIG. 1.

Referring to FIG. 1, a computed tomography (CT) imaging system 10 is shown as including a gantry 12 representative of a "third generation" CT scanner. The gantry 12 has an x-ray source 14 that projects a beam of x-rays 16 toward a detector array 18 on the opposite side of the gantry 12.

The detector array 18 is formed by a plurality of detection elements 20 which together sense the projected x-rays that pass through a medical patient 22. Each detection element 20 produces an electrical signal that represents the intensity of an impinging x-ray beam and hence, the attenuation of the beam as it passes through the patient 22. During a scan to acquire x-ray projection data, the housing 12 and the components mounted thereon rotate about a center of gravity.

The operation of the x-ray source 14 is governed by a control mechanism 26 of the CT system 10. The control mechanism 26 includes an x-ray controller 28 that provides power and timing signals to the x-ray source 14. A data acquisition system (DAS) 32 in the control mechanism 26 samples analog data from the detection elements 20 and converts the data to digital signals for subsequent processing. An image reconstructor 34 receives sampled and digitized x-ray data from the DAS 32 and performs high speed image reconstruction. The reconstructed image is applied as an input to a computer 36 which stores the image in a mass storage device 38.

Figure 3:
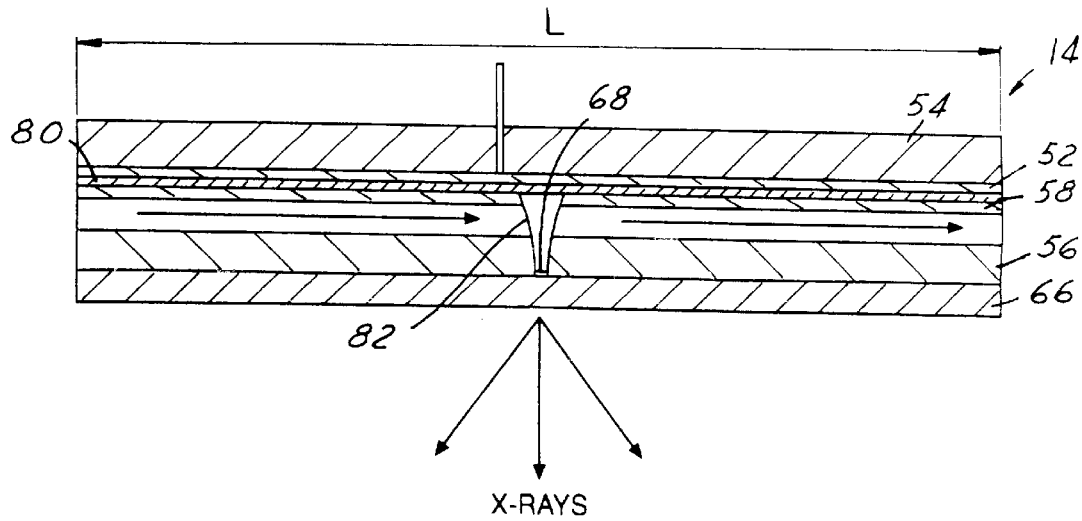
FIG. 3 is a cross-sectional view of a solid state x-ray tube according to the present invention.
Figure 4:
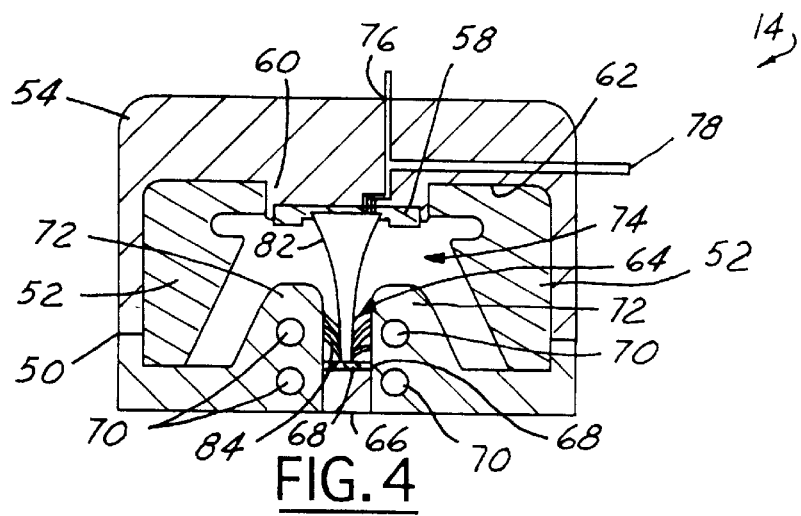
FIG. 4 is a cross-sectional view of an alternative embodiment according to the present invention.

The computer 36 also receives and supplies signals via a user interface or graphical user interface (GUI). Specifically, the computer 36 receives commands and scanning parameters from an operator console 40 that preferably includes a keyboard and mouse (not shown). An associated cathode ray tube display 42 allows the operator to observe the reconstructed image and other data from the computer 36. The operator supplied commands and parameters are used by the computer 36 to provide control signals and information to the x-ray controller 28, the DAS 32, and a table motor controller 44 in communication with a table 46 to control operation of and movement of the system components Referring now to FIGS. 3 and 4, a respective longitudinal cross-sectional view and lateral cross-sectional view of an x-ray source is illustrated. X-ray source 14 has a housing 50 that is sealed to provide a vacuum therein. Housing 50 has a support frame 52 positioned therein. Support frame 52 is preferably comprised of an insulative material such as alumina.

Housing 50 has a support portion 54 and a cooling block portion 56. Support portion 54 is preferably formed from an insulative material such as a high voltage epoxy compound. Various types of compounds would be evident to those skilled in the art. Cooling block portion 56 is thermally conductive and electrically conductive. Cooling block portion 56 is preferably formed of copper.

Support portion 54 is generally an elongated semi-tubular shape. As illustrated, support portion 54 is u-shaped. Support portion 54 is used to position a cathode 58 for generating electrons. Cathode 58 may be supported by a cathode support portion 60 which is integrally molded with support portion 54. Cathode support portion 60 extends a predetermined distance D from a back wall 62 of support portion 54. The distance D may be adjusted depending on the desired characteristics of the materials used and output desired.

Cooling block portion 56 has an elongated channel 64 or beam opening extending therethrough. Elongated channel 64 has an x-ray transmissive window 66 disposed therein. X-ray transmissive window 66 preferably completely fills elongated channel 64. X-ray transmissive window 66 is preferably formed from an electrically conductive material and a thermally conductive material such as a carbon-based material like graphite. Also, it is preferred that the atomic mass or "Z" of the x-ray transmissive window 66 is relatively low. Other suitable materials known to those skilled in the art include beryllium.

An anode 68 is formed directly and operatively adjacent to x-ray transmissive window 66. Preferably, anode 68 is formed of a thin metallic layer 68 or foil. The thin film anode 68 is preferably formed of a high atomic weight material such as tungsten or uranium. Of course, those skilled in the art will recognize that preferably the highest atomic weight material is used but there may be a trade-off between physical dimension, strength-to-weight ratio, and x-ray production. Anode 68 may be formed as a thin film which is deposited directly onto window 66. Because of the x-ray process, heat may be generated at anode 68 and therefore anode 68 is preferably thermally coupled to cooling block portion 56. Anode 68 may also be formed from a relatively thin layer of tungsten or tungsten alloy (2 to 30 microns) on a copper substrate.

Cooling block portion 56 preferably has a plurality of cooling tubes 70 extending therethrough. Cooling tube 70 provides cooling fluid or air therethrough to reduce the temperature of cooling block portion 56 and ultimately the temperature of anode 68. Preferably, cooling tube 70 extend substantially the length L of x-ray source 14. Elongated channel 64 is defined in cooling block portion 56 by shoulders 72 that extend in an inward direction toward cathode 58. As will be further described below, shoulders 72 help provide a conductive path for electrons passing through anode 68.

Support portion 54 and cooling block portion 56 define a vacuum chamber 74 therein. Vacuum chamber 74 preferably extends substantially the length of support portion 54 and cooling block portion 56 short of any end wall structures. Vacuum chamber 74 is preferably actively pumped so that the vacuum is always at an optimum level. This will reduce high voltage instabilities.

Cathode 58 has a plurality of gating connections 76 coupled thereto. Gating connections 76 control the turning on and off of cathode 76. High voltage input 78 is coupled to cathode 58 to provide the necessary potential for the generating of electrons. Both gating connections 76 and high voltage input 78 may be formed through support portion 54.

Cathode 58 is preferably formed of an elongated array of electron emitters. Various types of emitters may be used. For example, ferro-electric emitters may be used to create an electron emission in the form of a small, relatively narrow beam width that will impinge on anode 68. Another type of cathode that may be used is a thin film emission cathode. Such technology is similar to that used in flat panel monitors and television sets. Photo emitters may also be used for cathode 58. Photo emitters may, for example, use compact laser diode arrays. Emission occurs according to the order in which the laser beams of sufficient power and proper wavelength "address" the emitters by raster scanning of emitters which are arranged across a face of a flat panel plane or arranged on a bar that scans or moves across the face of the device. The photo emitters may also be in the form of a line or series of smaller dimension standalone emitter batches that would emit in a pattern corresponding to the emitters that have been addressed to be emitting. In all of the embodiments, cathode 58 may be formed of a plurality of emitters 80 best shown in FIG. 3. Cathode elements 80 are preferably addressable meaning that they may be selectively turned on and off to form the electron beam. With respect to emitters, photo emitters emit electrons when light reaches the solid state device capable of releasing the electrons into vacuum chamber 74. Light emission from photo laser devices such as solid state lasers and the like have been controlled to within micro or nano seconds. Laser devices can produce high efficiencies of photo emission. Preferably the addressability is sequential and allows the beam formed at one end to effectively move across the cathode in a scanned manner. Light signal switching devices such as micro-machined mirrors onto a solid state monolithic substrate may also be used. Light may also be delivered using a fiber optic or free beam means. For example, a six micro amp electron beam is produced for every milliwatt of laser light at 1% quantum efficiency using a gallium arsenide laser with 780 nanometer light where circular polarization is used for polarized electron delivery. Infrared laser bars are also commercially available in the 1 watt to 10 watt power range corresponding to 6 to 60 milliamps of electrons at 1% QE.

Those skilled in the art will recognize that polarized elections are not required in this invention. This corresponds to the efficiency of the photo emitters.

In operation, the desired emitters 80 are turned on as addressed to generate the desired beam 82. Preferably, electron beam 82 starts at one end of cathode and works its way across the cathode generating x-rays in a linear or sequentially moving manner. The electrons are released from cathode 58 and travel toward anode 68. When the electrons impinge upon anode 68, x-rays are released through window 66. Heat that formed in anode 68 is thermally coupled into shoulder 72 of cooling block portion 56. Heat may also be formed in window 66 which is also thermally conducted to cooling block 56. Heat is removed from cooling block 56 through cooling channel 70 which may be provided with cooling fluid or air.

It is possible for some electrons to travel through anode 68 and enter window 66. Because window 66 is preferably electrically conductive, electrons entering window 66 are electrically conducted to cooling block 56 and may re-enter beam 82 through shoulder 72. This is illustrated as stray electron paths 84. The paths 84 complete the electrical loop back to anode 68.

Preferably, the length of cathode 58, the length of anode 68, the length of window 66, and the length of elongated channel 64 are all substantially the same and are preferably just short of or about length L.

Figures 5A, 5B:
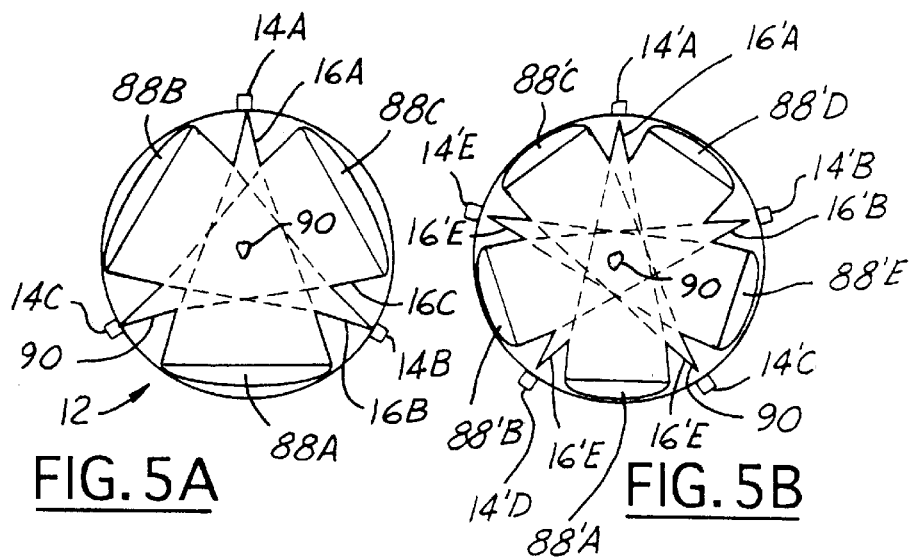
FIGS. 5A and 5B are diagrammatic views of a scan using multiple x-ray tubes and detectors according to the present invention.

Referring now to FIGS. 5A and 5B, an interior view of a gantry 12 is illustrated. In FIG. 5A, a first, second and third x-ray source 14A, 14B, and 14C are used to generate respective x-rays 16A, 16B, and 16C. Each of x-rays 16A, 16B, and 16C impinge upon a corresponding detector 88A, 88B, and 88C. By using a device without a rotating gantry, each of the x-ray sources 14A–14B, x-rays 16A–16B, and detectors 88A–88C are relatively fixed. In such an embodiment, the beams merely scan the length of the cathode without actually physically moving the x-ray source or detectors. In such a manner, the non-rotating complexity in prior known systems is substantially reduced. Also, such systems are believed to be substantially faster in the generation of an image.

Referring now to FIGS. 5A and 5B, five x-ray sources, 14'A–14'E are illustrated generating x-rays 16'A, 16'B, 16'C, 16'D, and 16'E toward detectors 88'A, 88'B, 88'C, 88'D, and 88'E in a segmented manner. Of course, those skilled in the art would recognize that a continuously tube formed according to the teachings herein could also be used. A heart 90 is used to illustrate that a CT system formed according to the present invention may be sized to be tailored for the organ or body part to be imaged. By the use of solid state components in the present invention, a large vacuum system and complicated beam deflection system is not required. A rotating anode target, filament heaters, motors and large complex support frames are also eliminated from the design. Such a system is also easier to service and is predicted to reduce downtime in the field.

Faster scan times because of the ease in scanning the beam may also be acquired. This allows for such imaging as cardiac imaging. Power levels are reduced because the system may be positioned closer to the patient. Because intensity falls off inversely with respect to the square of the distance from the patient. For example, it is predicted that by using the teachings of the present invention the diameter of the CT system may be reduced by 20% while the required current level may be reduced by 36%. By building small units tailored to the particular applications, such as brain scans or cardiac scans, better resolution, faster patient throughput and lower cost to specialist treatment centers may be provided.

The cold cathode technology is particularly useful for instant startup, long life and low power consumption with rapid switch on/switch off.

By providing the multiple beams as illustrated in FIGS. 5A and 5B, the temperatures under a given electron beam may be reduced and yet produce an overall higher system imaging power. The fixed position of the x-ray source allows the beams to be switched on and off in rapid succession to eliminate problems with x-ray scanner normally associated with CT systems.

In alternative embodiments, the anode may be formed in various manners, including an application of metal such as tungsten on a layer of copper. Other such anode assemblies may include a sandwich-type target using alternating layers of tungsten or rhenium and another material such as graphite. The size of the layers may be approximately 1 to 5 microns for the tungsten and can be sized to minimize the temperature of the focal spot and maximize x-ray output depending on the particular application. The graphite layers or other suitable materials will allow the passage of electrons and x-rays.

The present invention allows conventional convection cooling due to the stationary anode. The large size of the target ring associated with such a device has a large surface area and thus the heat transfer coefficient does not need to be extremely high. Also, the beam fan angle may be decreased in particular applications to decrease the focal spot temperature.

Figure 6:
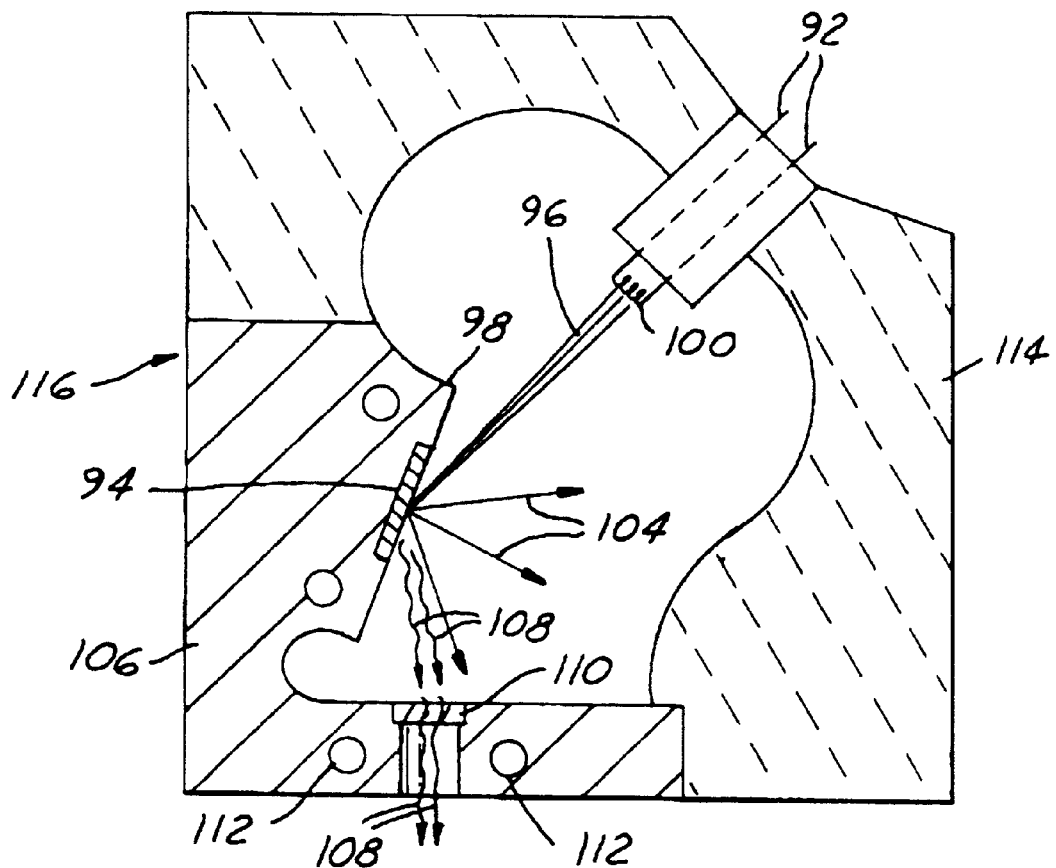
FIG. 6 is a cross-sectional view of an alternative embodiment of the present invention.

Referring now to FIG. 6, an alternative embodiment of a cylindrical tube around a center line 91 is shown in cross section. In this embodiment, cathode 92 is positioned at an angle relative to anode 94. That is, an electron beam 96 from cathode 92 hits anode 92 at a predetermined angle range of 15–60 degrees. In this illustration, 20 degrees is used. Cathode 92 may have a tungsten coil 100. However, cathode 92 may be also be formed of a cone-shaped field emitter, a hollow cylinder emitter, a carbon nanotube emitter, a photo emitter or other type of emitter known to those in the art. The type of emitter may depend on the particular system application or performance requirements. Anode 94 may, for example, be a patch of tungsten or rhenium. The backscattered electrons 104 strike part of anode 94 as well as copper cooling plate 106. Lines 108 indicate X-rays generated from anode 94. Cooling block 106 has an X-ray transmissive window 110, preferably formed of beryllium (Be) and coolant channels 112. The anode 94 and cathode 92 are separated in space and potential by insulator 114 which forms a portion of a housing 116 together with cooling block 106. The anode 94 in this embodiment is operatively coupled to window 110 but is separated therefrom, in contrast to the previous embodiment.

While the invention has been described in connection with one or more embodiments, it should be understood that the invention is not limited to those embodiments. On the contrary, the invention is intended to cover all alternatives, modifications, and equivalents, as may be included within the spirit and scope of the appended claims.

What is claimed is:

1. An X-ray source assembly comprising:
    a vacuum housing;
    a cold cathode emitter disposed within said housing;
    a cooling block having a beam opening therethrough;
    an X-ray transmissive window disposed within said beam opening; and
    a stationary anode disposed within said housing spaced apart from said emitter and thermally coupled to said cooling block, said anode comprised of a thin metallic film.

2. An X-ray source assembly as recited in claim 1 wherein said X-ray transmissive window is composed of a carbon-based material.

3. An X-ray source assembly as recited in claim 1 wherein said X-ray transmissive window is electrically conductive.

4. An X-ray source assembly as recited in claim 1 wherein said X-ray transmissive window is electrically coupled to said cooling block.

5. An X-ray source assembly as recited in claim 1 wherein said cooling block comprises a cooling tube extending therethrough.

6. An X-ray source assembly as recited in claim 1 wherein said anode is disposed on said window.

7. An X-ray source assembly as recited in claim 1 wherein said cathode emitter comprises a plurality of photo emitters.

8. An X-ray source assembly as recited in claim 1 wherein said cold cathode emitter comprises a plurality of laser diodes.

9. An X-ray source assembly as recited in claim 1 wherein said cathode emitter comprises a monolithic semiconductor.

10. An X-ray source assembly as recited in claim 1 wherein said cathode emitter comprises a plurality of addressable emitter elements.

11. An X-ray source assembly as recited in claim 1 wherein said anode is positioned directly adjacent to said window.

12. An X-ray source assembly as recited in claim 1 wherein said anode comprises a tungsten layer.

13. An X-ray source assembly as recited in claim 1 wherein said tungsten layer is disposed on a copper substrate.

14. An X-ray source assembly comprising:
    a vacuum housing;
    an elongated cathode emitter array having a plurality of X-ray emitter elements disposed within said housing;
    an electrically, thermally conductive cooling block having an elongated beam opening therethrough, said beam opening corresponding to said elongated cathode emitter array;
    an elongated X-ray transmissive window disposed within said beam opening; and
    an elongated stationary anode disposed within said housing and spaced apart from said emitter, said anode comprised of a thin metallic film.

15. An X-ray source assembly as recited in claim 14 wherein said X-ray transmissive window is electrically conductive.

16. An X-ray source assembly as recited in claim 14 wherein said X-ray transmissive window is electrically coupled to said cooling block.

17. An X-ray source assembly as recited in claim 14 wherein said cathode emitter comprises a plurality of addressable emitter elements.

18. An X-ray system comprising:
    a gantry;
    a plurality of stationary detectors disposed within said gantry;
    a plurality of stationary X-ray sources disposed within said gantry opposite said plurality of stationary detectors, each one of said plurality of X-ray sources comprising,
    a vacuum housing;
    a cold cathode emitter disposed within said housing;
    a cooling block having a beam opening therethrough;
    an X-ray transmissive window disposed within said beam opening; and
    a stationary anode disposed within said housing and spaced apart from said emitter and thermally coupled to said cooling block, said anode comprised of a thin metallic film.

19. An X-ray source assembly as recited in claim 18 wherein said X-ray transmissive window is electrically conductive.

20. An X-ray source assembly as recited in claim 18 wherein said cathode emitter comprises a plurality of addressable emitter elements.

* * * * *